(12) United States Patent
Wong et al.

(10) Patent No.: US 6,960,166 B1
(45) Date of Patent: Nov. 1, 2005

(54) SPECULUM HAVING ULTRASOUND PROBE

(76) Inventors: Irwin Lane Wong, 10960 Phillips St., Tustin, CA (US) 92786; Harry Hatasaka, 3806 W. Blacksmith Rd., Park City, UT (US) 84098

( * ) Notice: Subject to any disclaimer, the term of this patent is extended or adjusted under 35 U.S.C. 154(b) by 0 days.

(21) Appl. No.: 10/288,623

(22) Filed: Nov. 5, 2002

(51) Int. Cl.[7] ............................................. A61B 1/303
(52) U.S. Cl. ...................................... 600/221; 600/463
(58) Field of Search ................................ 600/202, 203, 600/210, 215, 216, 220, 221, 222, 223, 246, 600/459, 463; 601/2; D24/135; 128/916

(56) References Cited

U.S. PATENT DOCUMENTS

| | | | | |
|---|---|---|---|---|
| 1,568,732 A | * | 1/1926 | Haslinger | 600/196 |
| 3,851,642 A | * | 12/1974 | McDonald | 600/212 |
| 4,300,541 A | * | 11/1981 | Burgin | 600/213 |
| 4,492,220 A | * | 1/1985 | Hayes | 600/203 |
| 4,742,829 A | * | 5/1988 | Law et al. | 600/461 |
| 4,757,821 A | * | 7/1988 | Snyder | 600/453 |
| 4,877,033 A | * | 10/1989 | Seitz, Jr. | 600/441 |
| 4,905,670 A | * | 3/1990 | Adair | 600/104 |
| 4,945,896 A | * | 8/1990 | Gade | 600/202 |
| 5,143,054 A | * | 9/1992 | Adair | 600/104 |
| 5,469,853 A | * | 11/1995 | Law et al. | 600/463 |
| 5,499,964 A | * | 3/1996 | Beck et al. | 600/220 |
| 5,624,439 A | * | 4/1997 | Edwards et al. | 606/45 |
| 5,833,611 A | * | 11/1998 | Tepper et al. | 600/462 |
| 6,210,330 B1 | | 4/2001 | Tepper | |
| 6,273,896 B1 | * | 8/2001 | Franck et al. | 606/130 |
| 6,309,349 B1 | * | 10/2001 | Bertolero et al. | 600/213 |
| 6,432,048 B1 | | 8/2002 | Francois | |
| 2002/0133060 A1 | * | 9/2002 | Doyle | 600/210 |
| 2003/0040737 A1 | * | 2/2003 | Merril et al. | 606/1 |
| 2003/0153850 A1 | * | 8/2003 | Davis et al. | 601/2 |
| 2003/0225313 A1 | * | 12/2003 | Borodulin et al. | 600/135 |

FOREIGN PATENT DOCUMENTS

WO  WO 9903399  * 1/1999  ............ A61B 8/00

* cited by examiner

*Primary Examiner*—Kevin Shaver
*Assistant Examiner*—David Comstock
(74) *Attorney, Agent, or Firm*—Donald E. Stout; Stout, Uxa, Buyan & Mullins, LLP

(57) ABSTRACT

A speculum is equipped with an ultrasound probe, for permitting ultrasound visualization during procedures, such as transcervical embryo transfer with In Vitro Fertilization, thus providing superior transvaginal ultrasonographic imaging without interference by the ultrasound probe with usual embryo transfer techniques, and without the need for an additional assistant. The probe may be disposed on either of the posterior blade and the anterior blade, depending upon physiological factors varying with each patient and procedure.

20 Claims, 4 Drawing Sheets

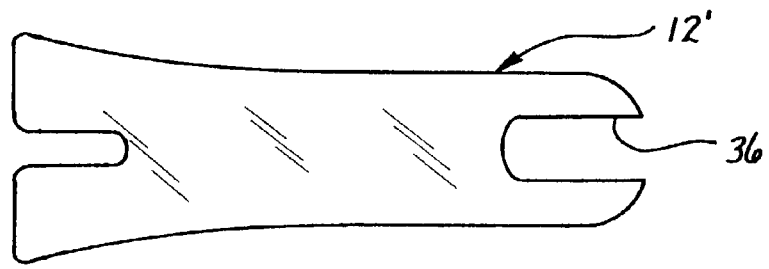
Fig. 4
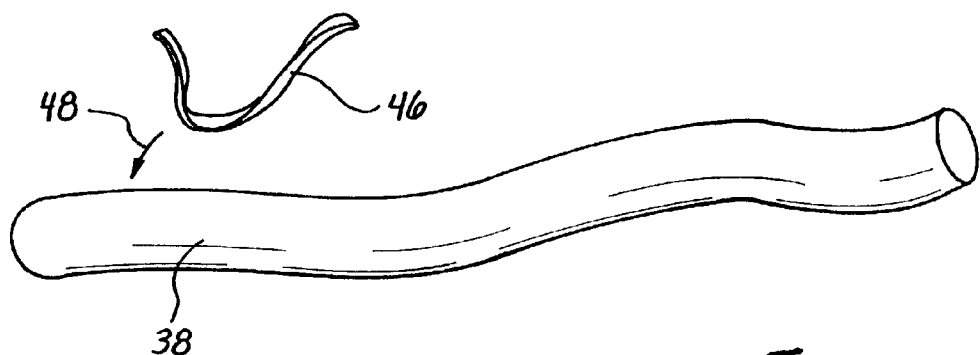
Fig. 5
Fig. 6
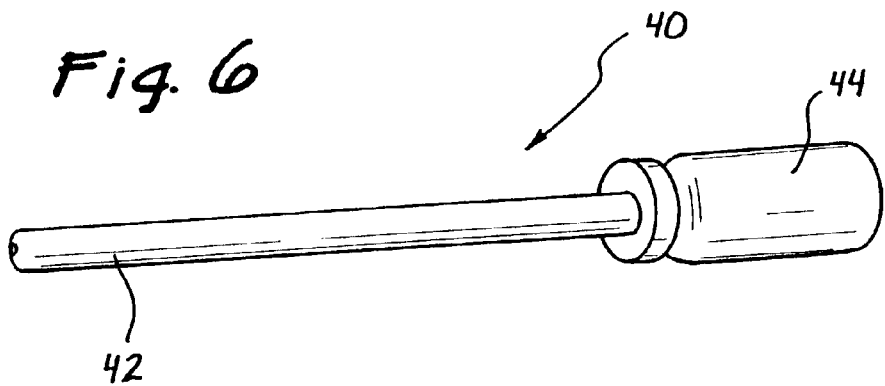

SPECULUM HAVING ULTRASOUND PROBE

BACKGROUND OF THE INVENTION

The present invention relates to methods and devices for performing medical procedures, including, but not limited to, gynecologic, otologic, neurosurigical, and gastrointestinal procedures, and move particularly to medical devices such as a speculum, having a built-in capability for permitting ultrasound visualization of a procedural site.

There are a number of gynecological procedures for which it would be advantageous to have the capability of direct transvaginal ultrasound visualization, for the purpose of permitting the medical practitioner to guide catheters and other instruments into the cervical canal and uterine cavity. For example, with the common infertility treatment known as In Vitro Fertilization (IVF), the crucial last step is the transfer of the fertilized eggs (embryos) through the cervix into the uterine cavity. This step is identified in the practice as transcervical embryo transfer. Embryos are usually transferred by first placing a speculum into the vagina to visualize the cervix. Then, a catheter containing the embryos at its tip is threaded through the cervix into the uterine cavity. The embryos are then released. Embryo transfers are thus commonly performed by feel. The catheter tip is felt to thread its way through the cervix into the uterine cavity.

Ultrasound visualization of the catheter as it traverses the cervix into the uterine cavity would provide many advantages. Ultrasound visualization would facilitate catheter negotiation of a difficult tortuous cervical canal, for example, and would allow more precise placement of the catheter tip within the uterine cavity. There are clinical studies which argue that more precise placement of the embryos in the uterine cavity improves pregnancy rates. Clinical studies also indicate that, using current techniques, some embryos may be inadvertently placed within the cervical canal. Ultrasound visualization would help to ensure the release of embryos into the uterine cavity. Embryos themselves are too small to visualize, but they can be placed adjacent to two small air bubbles in the catheter, subsequent to which the air bubbles can easily be detected by ultrasound imaging techniques.

In the current state of the art, ultrasound visualization of the cervix and uterus can be accomplished in three ways. One way is to place an ultrasound probe, of known construction, on the abdomen of the patient. This transabdominal approach makes it very difficult to adequately visualize the cervical canal and uterine cavity. This problem is worsened in the case of obesity, deep retroverted and retroflexed positions of the uterus, suboptimally positioned uteri, and intervention of the bowel between the skin and the uterus. The pubic bone can also obstruct visualization. The transabdominal approach usually requires a full, uncomfortable bladder for optimal visualization of the cervical canal and uterine cavity. The transabdominal approach also requires two people, one to hold the abdominal ultrasound probe in the best orientation for cervical canal and uterine cavity visualization, and the other to do the actual transfer, which includes threading the catheter through the cervical canal and into the uterine cavity, as well as releasing the embryos. Thus, the sonographic image of the cervical canal and the uterine cavity obtained by the transabdominal probe is more uncomfortable and usually inferior in quality to that obtained by use of the transvaginal probe. Nonetheless, transabdominal ultrasound is the visualization method most often employed with embryo transfers because it does not interfere with the normal procedure of embryo transfer.

The second visualization approach which is currently employed is transvaginal ultrasound. This approach provides an improved visualization of the cervical canal and uterine cavity relative to transabdominal ultrasound, but interferes with the most common embryo transfer techniques by virtue of the ultrasonic probe being physically present in the vagina. Suboptimal ways around this problem include:

1) Placing the speculum in the vagina first. Then, the catheter is threaded through the cervix and into the uterine cavity by feel. While holding the catheter in position, the speculum is removed. The transvaginal probe is then placed into the vagina while still holding the catheter in place, while hoping that the probe's placement will not disturb the catheter's placement unduly.

2) Placing the speculum in the vagina first. Then, the catheter is threaded through the cervix and into the uterine cavity by feel. While holding the catheter, and with the speculum still in place, an assistant places the transvaginal probe into the vagina. This awkward method thus requires two people, one to hold the transvaginal probe in position to obtain visualization of the cervical canal and uterine cavity, and the second to hold the catheter, and then, while the catheter tip is in the optimum position, to depress the syringe attached to the catheter and thus release the embryos.

3) Placing the speculum in the vagina first. Then, the transvaginal probe is placed through the speculum into the vagina. Finally, an attempt is made to thread the catheter through the external cervical os into the uterine cavity while the transvaginal probe is also within the speculum. This approach is very difficult because the probe within the speculum physically and visually blocks access to the external cervical os.

As is obvious from the above descriptions, each of these described suboptimal approaches creates difficulty and unnecessary complications, thereby reducing the opportunity for a successful outcome.

Yet a third visualization approach sometimes employed in certain procedures is transrectal ultrasound, but this technique for visualization is cumbersome, compromising, and uncomfortable.

What is needed, therefore, is a visualization approach which allows the best of both worlds; i.e. superior transvaginal ultrasonographic imaging without interfering with typical medical procedures, such as transcervical embryo transfer, hysteroscopic procedures, and the like.

SUMMARY OF THE INVENTION

The present invention solves the foregoing problems by providing a speculum equipped with an ultrasound probe, for permitting ultrasound visualization during gynecological procedures, such as IVF. The inventive system provides the best of both worlds; i.e. superior transvaginal ultrasonographic imaging without interference by the ultrasound probe with usual embryo transfer techniques, and without the need for an additional assistant. In other words, the inventive device provides a speculum which has the capability of providing simultaneous hands-free sonographic information by integrating the sonographic probe with the speculum. Thus, the inventive speculum, with integrated ultrasound probe permits physical access to a procedural site, and simultaneous real-time sonographic visualization of the site, as well as allowing the operator to have two hands free to interact with the site, e.g. to perform a transcervical transfer of embryos into the uterine cavity.

In its broadest aspect, the invention provides a physical self-retaining device for separating tissue, into which an ultrasound imaging capability has been incorporated. This unique combination provides an ability to physically and visually access a procedural site with simultaneous sonographic imaging and both of the practitioner's hands free to operate on the site.

More particularly, there is provided, in one aspect of the invention, a speculum comprising a member for separating tissue at a procedural site within a body of a patient, and a visualization device disposed on the member. In a preferred embodiment, the aforementioned member comprises one of a posterior blade and an anterior blade, and the visualization device comprises, preferably, an ultrasound visualization device, and most preferably an ultrasonic probe, disposed on the member. The determination as to whether the probe is to be disposed on the posterior or the anterior blade is made dependent upon physiological factors, primarily the orientation of the uterus.

In a preferred embodiment, the blade on which the visualization device is disposed includes structure for accommodating the visualization device. This accommodating structure comprises, in one embodiment, a recess disposed on a distal portion of the blade. In another embodiment, a notch is provided for accommodating the ultrasonic probe, which may be adapted to engage the notch by means of a snap fit. A power cord extends proximally from the visualization device, and in a preferred embodiment, structure is provided for securing the power cord to the blade on which the visualization device is disposed. This structure may include one or both of a channel disposed along a portion of a length of the blade, and a clamp.

Because it is desirable to be able to maneuver the ultrasonic probe relative to the speculum, during the medical procedure, in one preferred embodiment the blade on which the visualization device is disposed comprises a distal portion which is pivotally attached to a remaining blade portion. The visualization device is disposed on this distal blade portion.

In another aspect of the invention, there is provided a speculum comprising a first blade, a second blade, a handle, and an ultrasound probe disposed on one of the first and second blades. In a preferred embodiment, the first and second blades are posterior and anterior blades, respectively. A groove is preferably provided on the ultrasound probe for engaging a portion of the blade on which the probe is disposed, in order to secure the probe to the blade.

In still another aspect of the invention, there is taught a method of performing a gynecological medical procedure, comprising steps of securing an ultrasound probe to one of an anterior or posterior blade of a speculum, providing electric power to the probe, inserting the speculum into a patient's vagina and viewing images supplied by the ultrasound probe to suitable ultrasonic viewing equipment in order to guide movements of the speculum and other desired medical instruments. A preferred method additionally comprises a step of preliminarily examining the patient to determine an orientation of the patient's uterus. The inventive apparatus has the capability for being modified by the practitioner to the extent that the practitioner may selectively secure the ultrasound probe to either one of the anterior or posterior blades, and the inventive method provides that this step includes a step of determining to which blade the ultrasound probe is to be secured based upon the results of the aforementioned preliminary examination step. In a preferred method, the practitioner may also dispose a sterile cover over the ultrasound probe.

The invention, together with additional features and advantages thereof, may best be understood by reference to the following description taken in conjunction with the accompanying illustrative drawing.

BRIEF DESCRIPTION OF THE DRAWINGS

FIG. 4 is a top view of a speculum blade, which has been adapted, in accordance with principles of the present invention, to receive an ultrasonic probe for securement therewith;

FIG. 5 is a perspective view of a sterilized transvaginal ultrasound transducer cover for use in connection with the present invention, together with a sterilized twist tie;

FIG. 6 is a perspective view of an ultrasound gel applicator for use in connection with the present invention;

DESCRIPTION OF THE PREFERRED EMBODIMENT

Figure 1:
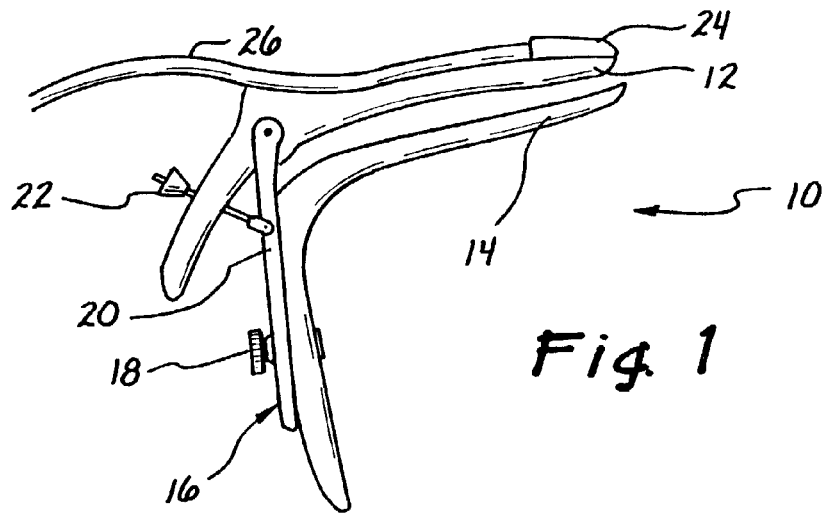
FIG. 1 is a plan view, from the side, of one embodiment of the present invention, comprising a speculum having an ultrasonic probe attached thereto.

Now with reference more particularly to the drawing figures, there is shown in FIG. 1 a first embodiment of a medical instrument or speculum 10 constructed in accordance with the principles of the present invention. For purposes of defining terminology in the appended claims, the term "speculum" is broadly defined as a physical device for separating tissue to allow visualization of an internal bodily structure, such as the cervix. The speculum 10 in the illustrated preferred embodiment may be of a generally conventional design, except as described below, and comprises an anterior (upper) blade 12, as well as a posterior (lower) blade 14. As is well known in the art, the two opposed blades 12, 14 are movable between a closed position for insertion and withdrawal, and an open position for performing a pelvic examination or procedure. A downwardly depending handle portion 16 operates to effect blade movement, as desired, in a manner also well known in the art. A screw 18 on the handle portion 16 secures the upper and lower blades 12, 14 together, and a lever 20 separates the two blades. A locking screw 22 is provided to fix the blades 12, 14 in position, as desired.

Advantageously, in accordance with the principles of the present invention, an electronic vaginal ultrasound probe or transducer 24 is disposed on the anterior blade 12. The transducer 24 is powered by means of a power cord 26 which is connected to a suitable source of power (not shown). The ultrasonic transducer 24 may be a commercially available product, such as, for example, finger tip type probes such as the Hitachi EUP-F331 or EUP-F334, which, although not optimal, can be customized sufficiently to permit their attachment to the blade 12. Alternatively, a completely customized transducer 24 may be employed, although it may utilize conventional ultrasound imaging technology. Importantly, the probe 24 and cord 26 should be as small as practicable, in order to maximize visualization and access to the cervical ostium for introduction and placement of required instruments, such as catheters and the like, through the limited vaginal space.

Figure 2:
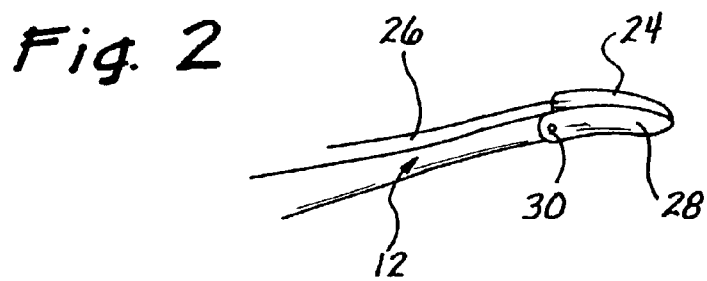
FIG. 2 is a plan view of a modified hinged portion of the embodiment of FIG. 1.

Ideally, it is desirable that the direction of the sound beam emanating from the transducer 24 be adjustable to optimize visualization of the cervical canal and uterus. This objective may be achievable using a probe with a digitally enhanced scanning field and adjustable scanning field of view available on some ultrasonic imaging systems. Another option is to employ a spiral cervical retractor, such as the instrument sold under the trademark RETRAX, when necessary, for the most noninvasive and efficacious canulation of the cervical/endometrial canal possible. Such an instrument allows the practitioner to adjust the angle of the cervical canal to facilitate catheter placement. Alternatively, as shown in FIG. 2, a distal hinged portion 28 of the blade 12 may be utilized, wherein the blade portion 28 is pivotally attached to the remaining blade portion by means of a hinge 30. With such an arrangement, the direction of the vaginal transducer sound beam can be physically adjusted while the speculum 10 is in place in the vagina. Still another possibility, in order to provide a capability for rotation of the transducer 24 in the event of an off-axis uterus, for example, is to use a speculum having a low angle handle, rather than a 90 degree angle handle, to allow partial rotation of the entire speculum along with the transducer fixed and attached to it.

It should be noted that the orientation of the speculum 10 as shown in FIGS. 1 and 2 is suitable for visualization of an anteverted or anteflexed uterus. For a retroverted or retroflexed uterus, as is known to skilled practitioners, the ultrasound speculum 10 is rotated as much as 180 degrees.

Figure 3:
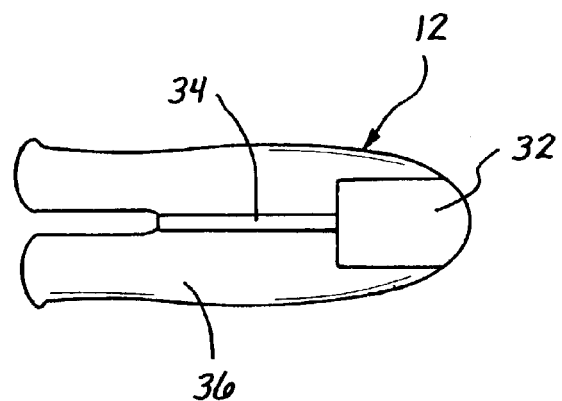
FIG. 3 is a top view of the speculum of FIG. 1.

Now, with particular reference to FIG. 3, there is shown a top view of the anterior blade 12. In the illustrated embodiment, a recess or cradle 32 is provided in a distal end of the blade 12 for accommodating the ultrasonic transducer 24 (not shown in FIG. 3). Additionally, a channel 34 is disposed longitudinally along a portion of the blade 12, for accommodating the transducer power cord 26 (also not shown in FIG. 3). The recess 32 and channel 34 together result in a relatively flush top blade surface 36, even when the transducer 24 and power cord 26 are installed on the blade 12, thus improving ease of operation and maneuverability of the instrument.

The transducer 24 may be secured to the blade 12 using any suitable fixation means, including elastic bands, adhesive, mechanical fasteners, and the like. Similarly, the cord 26 may be secured within the channel 34 by any suitable means, such as the presently preferred elastic band. Alternatively, in some applications, there may be no need to secure the cord, other than the ensure that it lies within the channel 34.

Referring now to FIG. 4, there is shown a modified embodiment of the anterior blade 12' of the speculum 10, wherein a notch 36 is formed at its distal end for accommodating the transducer 24. In this embodiment, no cord channel is shown, although one could be utilized, if desired. Whereas the embodiments shown to this point have all been anterior blade installations, as will be described hereinbelow, posterior blade installations are contemplated as well. Thus, the posterior blade 14 may be provided with an identical recess 32 or notch 36, as well as cord channel 34. Smooth removable notch covers (not shown), may be employed to cover the notch 36 in the event that the blade 12' or 14 does not require an ultrasonic transducer 24.

In this notch embodiment of FIG. 4, wherein the notch extends completely through the blade, unlike the recess 32, it is preferred that the transducer head 24 snap or slide into place within the notch.

In FIG. 5 there is illustrated a sterilized transvaginal ultrasound transducer cover 38, for covering the transducer head 24 and permitting ultrasound gel to be retained therearound. A plastic ultrasound gel applicator 40 (FIG. 6), having a long tubular dispenser 42 and a proximal squeezable gel container 44 may be utilized to dispense the ultrasound gel into the cover 38. Standard sterilized twist ties 46 (FIG. 5) may be employed, just behind the transducer head 24, as shown by the arrow 48 in FIG. 5, to retain the gel around the transducer, thereby allowing good visualization of the uterus and its canal.

The sterile cover 38 of FIG. 5 is useful, for example, in a case where the practitioner needs to perform multiple procedures in sequence. In the earlier mentioned IVF treatment, for example, the practitioner may need to effect multiple sequential embryo transfer. Rather than sterilizing the transducer 24 separately, prior to each transfer, thereby slowing down the flow of the procedure, the cover 38 need only be quickly changed out. Cover 38 may be placed on the anterior and posterior blades, thus allowing multiple uses of the speculum 10 without sterilization. Alternatively, if multiple speculums are available, cover 38 need only be used over the ultrasound probe and the speculum then is changed between patients.

Another problem in an IVF procedure is that there will be air in the patient's vagina with the speculum open. This condition may significantly disrupt transvaginal visualization. However, utilization of the ultrasound gel within the cover 38 negates that concern.

Figure 7:
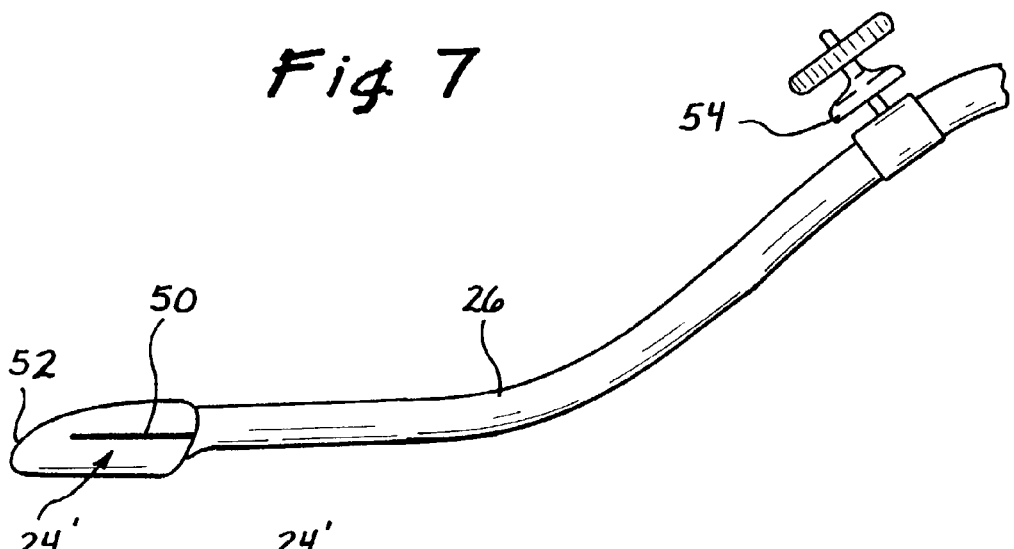
FIG. 7 is a perspective view of a modified ultrasound transducer which may be used in connection with a speculum, in accordance with the principles of the present invention.
Figure 8:
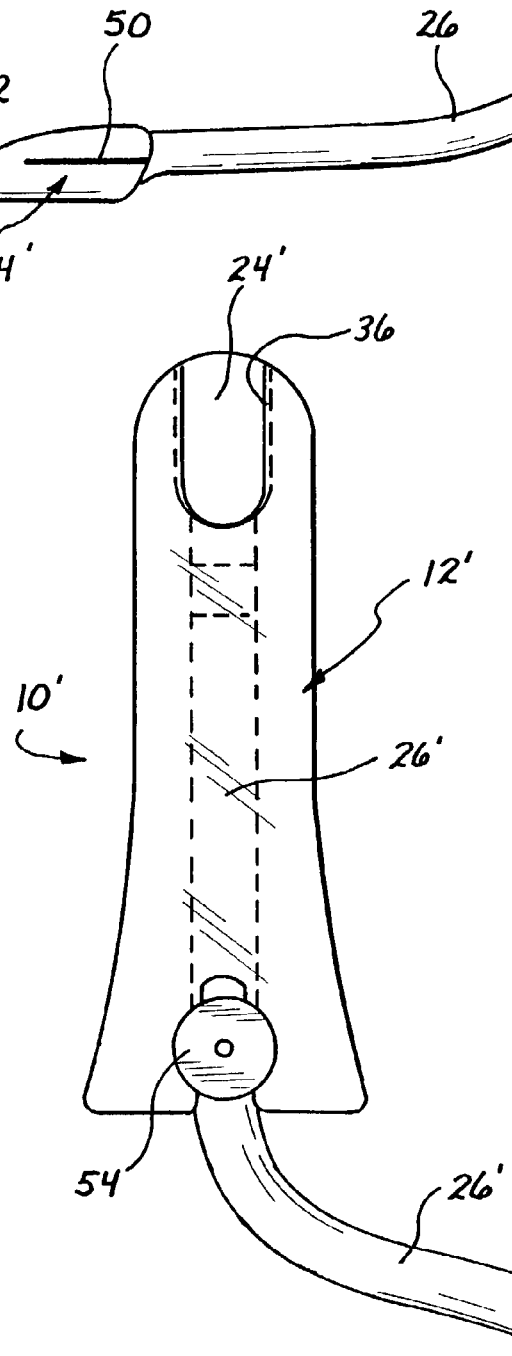
FIG. 8 is a top view of a modified embodiment of the ultrasonic speculum of the present invention.

FIG. 7 illustrates in greater detail the transducer 24 and power cord 26, and particularly the transducer 24 wherein it has been modified by the addition of a groove 50, for the purpose of sliding or snapping the transducer 24 into the notches 36, as discussed above. The tip 52 of the transducer 24 is preferably plastic, and conforms in configuration to the curved angles of the speculum so that it will slide in smoothly with vaginal placement of the speculum. In the event a cord channel 34 is not employed, such as is the case for the anterior blade 12' of FIG. 4, a sliding clamp 54 may alternatively be employed, to affix the cord to the anterior speculum blade 12', thus avoiding an obstructed field of vision due to a free-floating cord 26. Yet another alternative is to employ both the cord channel 34 and cord clamp 54, for additional security. A top view of an embodiment of the speculum 10' which includes the cord 26 and transducer 24 of FIG. 7 is illustrated in FIG. 8.

In a modified embodiment of the speculum, there may be disposed a cord retainer (not shown) on the left and right aspect of the blade or handle, such that the cord can be positioned away from the midline, to the left or right. This retainer may take the form of a channel or hook, or other suitable means, for engaging and keeping the cord in position.

Figure 9:
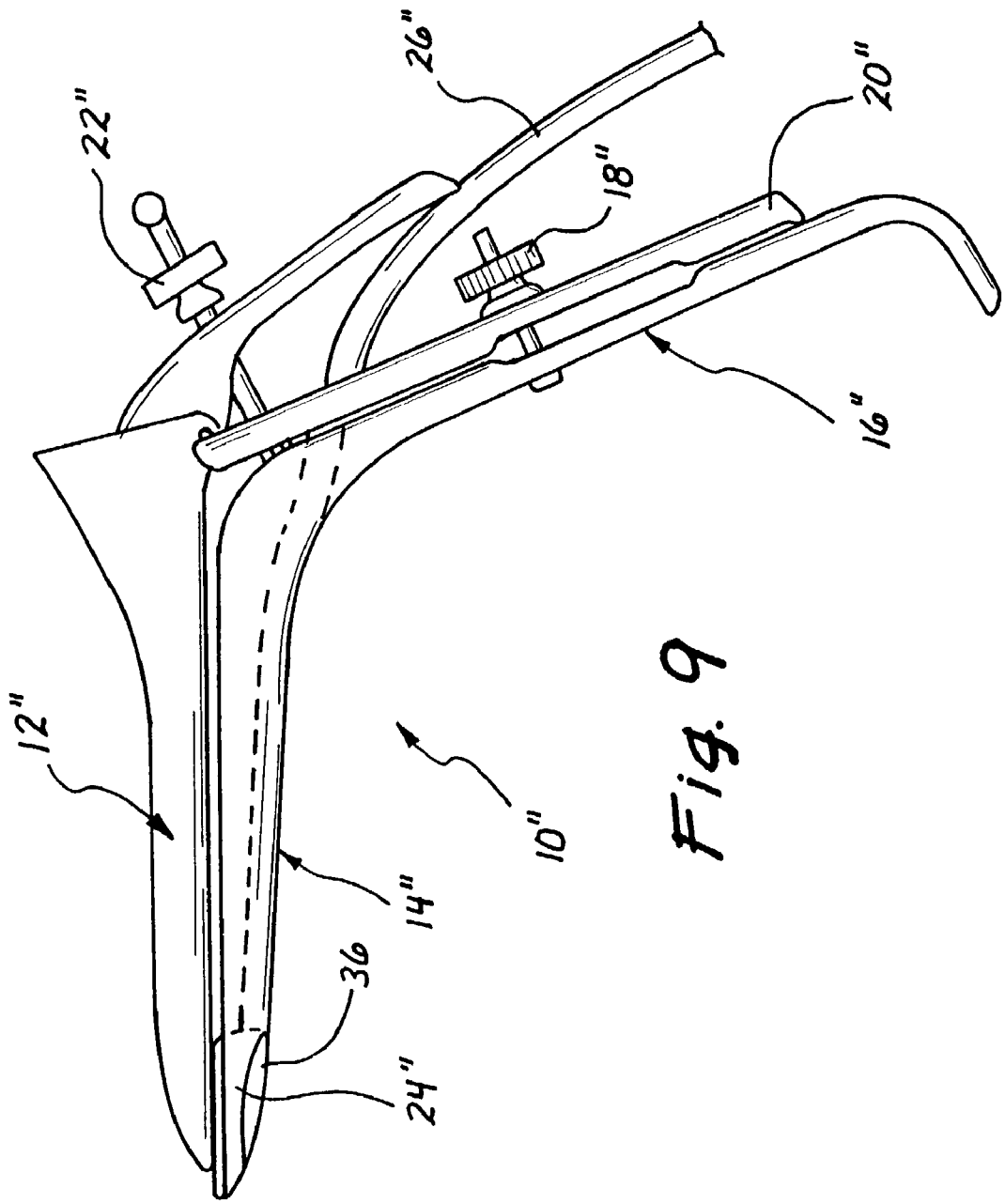
FIG. 9 is a lateral plan view of another modified embodiment of the present invention, wherein the ultrasonic probe is disposed in the posterior rather than anterior speculum blade.

FIG. 9 is a lateral plan view of yet another modified embodiment of the ultrasound speculum 10" of the present invention, wherein the ultrasound transducer 24 is disposed on the posterior (lower) blade 14", rather than the anterior (upper) blade 12", as in the earlier described embodiment. The speculum 10" may be in all respects similar in construction to the speculum 10 of FIG. 1, or the speculum 10' of FIG. 8, except for the change in location of the transducer 24" from the anterior blade 12" to the posterior blade 14". The blade 14" may be constructed in a manner similar to the blade 12 in either of the earlier described embodiments, i.e. with an accommodating recess 32 or notch 36" for receiving the transducer 24". Additionally, a cord channel 34 and cord clamp 54 may or may not be utilized, either singly or in combination.

In the case of mid to anteverted uteri, an anterior blade ultrasound transducer location is generally indicated for easier visualization. However, if the uterus is retroverted, the anterior blade location would prevent the ultrasound pulses from bouncing back to the transducer 24, and thus hamper visualization of the cervical canal, because the posterior blade will tend to block the angle of the ultrasound pulses. Accordingly, the posterior blade location illustrated in FIG. 9 is indicated for retroverted uteri, resulting in an improved orthogonal angle for maximum canal resolution. The invention contemplates, as discussed above, the availability of ultrasound speculums having the capability of being readily configured for either an anterior or posterior blade location by the practitioner, after initial examination of the patient.

While the foregoing invention has been particularly discussed in connection with the IVF procedure, it is appropriate as well for many other gynecological procedures, such as hysteroscopic procedures. For example, with hysteroscopic fibroid removal, ultrasound will detect fibroids not apparent by visual hysteroscopic examination. Also, ultrasound is able to aid in the removal of the visually nonapparent but sonographically discernible intramural portion of a fibroid. Other conditions and procedures appropriate for use with the inventive ultrasound speculum include cervical stenosis, difficult cervical dilatations, D & C's, intrauterine device (IUD) placement and removal, intrauterine adhesions, and vaginal, cervical, and uterine anomalies and gynecological tumors. For example, in treating a badly scarred cervix with trapped blood in the uterine cavity (hematometra), the inventive speculum will permit dilation of the true cervical canal (as opposed to a false passage) and guide evacuation of the trapped blood. Other uses include gynecologic procedures (suspension procedures) as well as for simultaneous use during laparoscopy and other abdominal procedures to help guide the operators. Also, the device may facilitate vaginal obstetric procedures, such as cerclage placement and chorionic villus sampling, and removal of retained placental fragments.

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A speculum comprising:
    a posterior blade and an anterior blade for separating tissue at a procedural site within a body of a patient; and
    an ultrasound visualization device disposed on one of said posterior blade and said anterior blade, said ultrasound visualization device being substantially smaller than said blades for separating tissue;
    wherein the blade on which said ultrasound visualization device is disposed includes structure for accommodating said ultrasound visualization device, said accommodating structure comprising a recess disposed on a distal portion of the blade on which said ultrasound visualization device is disposed.

2. The speculum as recited in claim 1, wherein said ultrasound visualization device comprises an ultrasound probe.

3. The speculum as recited in claim 1, wherein said ultrasound visualization device is disposed on said anterior blade.

4. The speculum as recited in claim 1, wherein said ultrasound visualization device is disposed on said posterior blade.

5. The speculum as recited in claim 1, wherein a power cord extends proximally from said ultrasound visualization device.

6. A speculum comprising:
    a posterior blade and an anterior blade for separating tissue at a procedural site within a body of a patient; and
    an ultrasound visualization device disposed on one of said posterior blade and said anterior blade, said ultrasound visualization device being substantially smaller than said blades for separating tissue;
    wherein the blade on which said ultrasound visualization device is disposed includes structure for accommodating said ultrasound visualization device, said accommodating structure comprising a notch disposed on a distal portion of the blade on which said ultrasound visualization device is disposed.

7. A speculum comprising:
    a posterior blade and an anterior blade for separating tissue at a procedural site within a body of a patient;
    an ultrasound visualization device disposed on one of said posterior blade and said anterior blade, said ultrasound visualization device being substantially smaller than said blades for separating tissue; and
    a power cord extending proximally from said ultrasound visualization device, said speculum further comprising structure for securing said power cord to the blade on which said ultrasound visualization device is disposed.

8. The speculum as recited in claim 7, wherein said structure comprises a channel disposed along a portion of a length of the blade on which said ultrasound visualization device is disposed.

9. The speculum as recited in claim 7, wherein said structure comprises a clamp.

10. A speculum comprising:
    a posterior blade and an anterior blade for separating tissue at a procedural site within a body of a patient; and
    an ultrasound visualization device disposed on one of said posterior blade and said anterior blade, said ultrasound visualization device being substantially smaller than said blades for separating tissue;
    wherein the blade on which said ultrasound visualization device is disposed comprises a distal portion which is pivotally attached to a remaining blade portion, said ultrasound visualization device being disposed on said distal blade portion.

11. A method of performing a gynecological medical procedure, comprising:
    securing an ultrasound probe to a speculum;
    providing electric power to said probe;
    inserting said speculum into a patient's vagina;
    viewing images supplied by said ultrasound probe to suitable ultrasonic viewing equipment in order to guide movements of said speculum and other desired medical instruments; and
    preliminarily examining the patient to determine an orientation of the patient's uterus.

12. The method of claim 11, and further comprising a step of securing the ultrasound probe to one of an anterior or posterior blade of said speculum.

13. The method of claim 12, wherein the step of securing the ultrasound probe to one of an anterior or posterior blade includes a step of determining to which blade to secure the ultrasound probe based upon the results of said preliminary examination step.

14. The method of claim 11, and further comprising disposing a sterile cover over said ultrasound probe.

15. A speculum comprising:
   a posterior blade and an anterior blade for separating tissue at a procedural site within a body of a patient; and
   an ultrasound visualization device disposed on one of said posterior blade and said anterior blade;
   the blade on which said ultrasound visualization device is disposed including structure for accommodating said ultrasound visualization device, said structure comprising a recess disposed on a distal portion of said blade.

16. A speculum comprising:
   a posterior blade and an anterior blade for separating tissue at a procedural site within a body of a patient; and
   an ultrasound visualization device disposed on one of said posterior blade and said anterior blade;
   the blade on which said ultrasound visualization device is disposed including structure for accommodating said ultrasound visualization device, said accommodating structure comprising a notch disposed on a distal portion of said blade.

17. A speculum comprising:
   a posterior blade and an anterior blade for separating tissue at a procedural site within a body of a patient;
   an ultrasound visualization device disposed on one of said posterior blade and said anterior blade;
   a power cord extending proximally from said ultrasound visualization device; and
   structure for securing said power cord to the blade on which said ultrasound visualization device is disposed.

18. The speculum as recited in claim 17, wherein said structure comprises a channel disposed along a portion of a length of the blade on which said ultrasound visualization device is disposed.

19. The speculum as recited in claim 17, wherein said structure comprises a clamp.

20. A speculum comprising:
   a posterior blade and an anterior blade for separating tissue at a procedural site within a body of a patient;
   an ultrasound visualization device disposed on one of said posterior blade and said anterior blade;
   wherein the blade on which said ultrasound visualization device is disposed comprises a distal portion which is pivotally attached to a remaining blade portion, said ultrasound visualization device being disposed on said distal blade portion.

* * * * *